Figure 1:
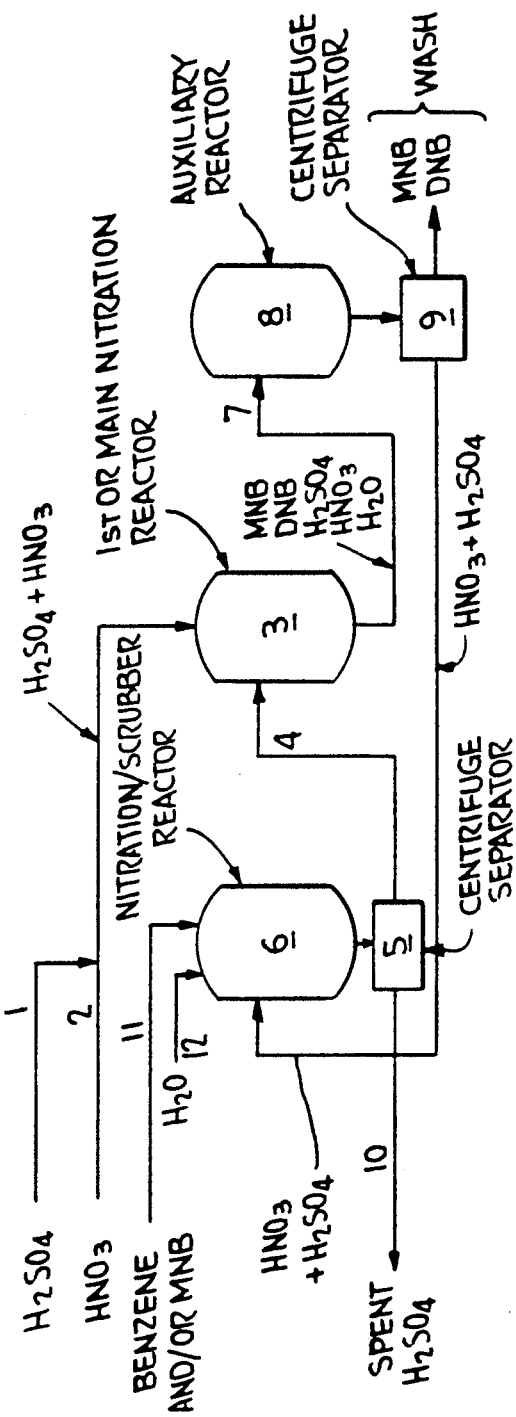

United States Patent [19]

Greenfield et al.

[11] Patent Number: 5,081,303

[45] Date of Patent: Jan. 14, 1992

[54] CO-PRODUCTION OF AN AROMATIC MONOAMINE AND AN AROMATIC DIAMINE DIRECTLY FROM BENZENE OR A BENZENE DERIVATIVE THROUGH CONTROLLED NITRATION AND REDUCTION

[75] Inventors: Harold Greenfield, Pascagoula; Arthur C. Bayer, Ocean Springs; Earl G. Alley, Starkville, all of Miss.

[73] Assignee: First Chemical Corporation, Pascagoula, Miss.

[21] Appl. No.: 341,743

[22] Filed: Apr. 21, 1989

[51] Int. Cl.$^5$ ............................................. C07C 206/36
[52] U.S. Cl. .................................... 564/419; 564/411; 564/420; 564/421; 564/422; 564/423
[58] Field of Search ............... 564/419, 411, 420, 421, 564/422, 423

[56] References Cited

U.S. PATENT DOCUMENTS

| | | | |
|---|---|---|---|
| 2,252,099 | 8/1941 | Rosen | 564/419 X |
| 3,356,729 | 12/1967 | Denton et al. | 564/423 |
| 3,472,897 | 10/1969 | Pryor et al. | 564/423 |
| 4,740,621 | 4/1988 | Adams et al. | 564/419 |

Primary Examiner—Richard L. Raymond
Attorney, Agent, or Firm—Breiner & Breiner

[57] ABSTRACT

A two-stage process for the co-production of aniline and m-phenylenediamine where, in the first stage, benzene, nitric acid, and sulfuric acid are reacted in a liquid phase to produce in greater amounts nitrobenzene (approximately 70%) and m-dinitrobenzene (approximately 30%), and in lesser or trace amounts o-dinitrobenzene and p-dinitrobenzene, and water; and in the second stage the products of the first stage are reacted with hydrogen in the liquid phase to produce aniline (approximately 70%) and m-phenylenediamine (approximately 30%) in greater amounts, and o-phenylenediamine and p-phenylenediamine in lesser amounts, and water. The reaction products are separated by distillation. The first stage of a preferred embodiment of the process is characterized in that a concentrated mixture of nitric acid and sulfuric acid are fed along with mononitrobenzene to a first reactor for producing dinitrobenzene, and then the dilute acid mixture recovered from this first reactor is fed along with benzene to a second reactor for producing the mononitrobenzene used as a reactant in the first reactor. The second stage, which provides the aniline and m-phenylenediamine, is characterized in that the hydrogenation is carried out in the liquid phase with the unpurified reaction products from the first stage.

Preferably, the second stage reaction is carried out utilizing a palladium-on-carbon catalyst in an amount of from 0.006 to 0.25 wt. % based on the total weight of the first stage reaction product mixture. The process is applicable to the co-production of other aromatic mono- and diamines.

23 Claims, 2 Drawing Sheets

CO-PRODUCTION OF AN AROMATIC MONOAMINE AND AN AROMATIC DIAMINE DIRECTLY FROM BENZENE OR A BENZENE DERIVATIVE THROUGH CONTROLLED NITRATION AND REDUCTION

RELATED APPLICATION

The present application is related to Ser. No. 793,788, filed Nov. 1, 1985, now U.S. Pat. No. 4,740,621.

FIELD OF INVENTION

This invention relates primarily to the co-production of an aromatic monoamine and an aromatic diamine directly from benzene or a benzene derivative through controlled nitration and hydrogenation. More particularly, this invention relates to a two-stage process for the efficient co-production of aniline and m-phenylenediamine by the direct nitration of benzene and subsequent reduction.

BACKGROUND OF INVENTION m-Phenylenediamine has been commonly produced by the reduction of m-dinitrobenzene. This process is relatively expensive in that the m-dinitrobenzene utilized is obtained through the complete dinitration of benzene which is then separated and purified prior to the reduction. This purification involves reaction with a substance such as sodium sulfite which places the undesirable o-dinitrobenzene and p-dinitrobenzene into an aqueous phase resulting in a large amount of waste water as disclosed, for example, in U.S. Pat. No. 3,086,063. The m-phenylenediamine must then be separated from reaction impurities after the reduction. m-Phenylenediamine has also been produced by reduction of dinitrobenzenes, followed by separation of m-phenylenediamine from o-phenylenediamine and p-phenylenediamine. Although less expensive than the above method, the dinitrobenzene utilized is obtained through complete dinitration of benzene which must be extracted or separated as a solid from the reaction medium.

More recently, U.S. Pat. No. 4,185,036 disclosed the hydrogenation of a mixture of an aromatic mononitro compound and an aromatic dinitro compound in the liquid phase. According to the process, hydrogen and a homogeneous or heterogeneous liquid mixture of at least 25 wt. % of an aromatic dinitro compound and/or at least 25 wt. % of a mononitro monoamino compound and at least 25 wt. % of an aromatic mononitro non-amino compound are reacted with vigorous mixing in the presence of a hydrogenation catalyst in an amount from 0.05 to 1.0 wt. % at a temperature of from about 75° to 225° C. and a pressure of about 50 to 800 psig. According to the patent, pure or relatively pure nitro products are used in the process as the starting materials to produce a mixture of the monoamino and diamino compounds which are then separated by distillation. The process is relatively expensive because of the need to separate and purify the starting materials and then the final products. Additionally, the process is relatively expensive because of the catalyst mixture employed.

OBJECTS AND GENERAL DESCRIPTION OF INVENTION

It is a primary object of the present invention to provide a process for the co-production of aniline and m-phenylenediamine which is relatively rapid an inexpensive.

It is another object of the invention to provide a two-stage process for the co-production of aniline and m-phenylenediamine directly from benzene and nitric acid without need for isolation and isomer purification of dinitrobenzene.

It is another object of the present invention to provide a method of producing m-phenylenediamine from benzene in a totally continuous process.

It is another object of the present invention to provide a process for the co-production of an aromatic monoamine and an aromatic diamine directly from benzene or a benzene derivative and nitric acid without need for intermediate isomer purification or separation.

It is another object of the present invention to provide a process for the co-production of an aromatic monoamine and an aromatic diamine directly from benzene or a benzene derivative and nitric acid without need for intermediate isomer purification or separation using a catalyst in nominal amount in relation to the total weight of the reaction mixture while maintaining an efficient reaction time and reasonable cost.

The above and other objects of the invention will be apparent from the following general description and the detailed presently preferred embodiments.

In accordance with the present invention, in a first stage benzene is reacted with nitric acid in the presence of sulfuric acid in the liquid phase to produce mononitrobenzene and m-dinitrobenzene in greater amounts, and o-dinitrobenzene and p-dinitrobenzene in lesser or trace amounts. This first stage is characterized in that in a preferred embodiment the benzene is nitrated in two reactors. In the one reactor benzene is converted to mononitrobenzene, and in a second reactor about 40% to 20% of the mononitrobenzene is converted to dinitrobenzene. The percentage converted to the dinitrobenzene is not critical. It is desirable that the percent converted is below the amount where crystallization of the dinitrobenzene will occur. At this stage of the nitration the dinitrobenzene is soluble in the mononitrobenzene which is at a point near a eutectic in the freezing point curve of the mononitro and dinitrobenzene. This is especially beneficial since the nitration can be carried out in one step without extra extraction or without an added solvent. It is noted, however, that at even this relatively low level of nitration the formation of the dinitrobenzene is a slower reaction requiring more strenuous conditions than is the formation of the mononitrobenzene. Accordingly, in a disclosed preferred embodiment of the process a strong or concentrated mixture of nitric and sulfuric acid is fed to the dinitration reactor for the formation of the dinitrobenzene from mononitrobenzene. The dilute acid by-product of the dinitration reaction containing a mixture of nitric and sulfuric acids and a small amount of dinitrobenzene is fed to the mononitration reactor where it is mixed with additional sulfuric and nitric acid, and reacted with benzene to form the mononitrobenzene. There is, therefore, a counterflow of mononitrobenzene and dinitration by-product acid between the two reactors. This counterflow is advantageous in that, since mononitration needs a less concentrated acid, the same sulfuric acid is used in each reactor; and, also, dinitrobenzene dissolved in the dinitration by-product acid is extracted with benzene and mononitrobenzene and recycled through the system. In an alternative embodiment, mononitrobenzene is the starting material and is nitrated to a 40% to 20% solution of dinitrobenzene. This alternative method does not have the benefits outlined for the counterflow method. As another modification of these embodiments, auxiliary reactors can be used downstream of the main reactor to improve efficiency of the dinitration and mononitration reactions.

The reaction mixture of mono- and dinitrobenzenes, without dinitrobenzene separation or isomer purification, is subjected in a second stage to hydrogenation in the liquid phase in the presence of a catalyst. The products of the reaction are aniline in the major amount, m-phenylenediamine in a lower amount, and the o-phenylenediamine and p-phenylenediamine in trace amounts. Additionally, the efficiency of the second stage is increased by utilizing a palladium-on-carbon catalyst. Only a low concentration of the palladium-on-carbon catalyst is required to produce a highly efficient reaction rate and a substantial yield of the desired products. The products of the reaction are separated by distillation. The reaction proceeds as follows:

First Stage:

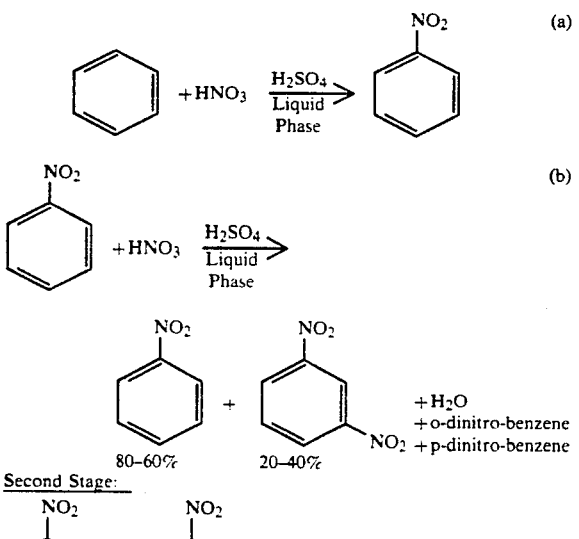

Second Stage:

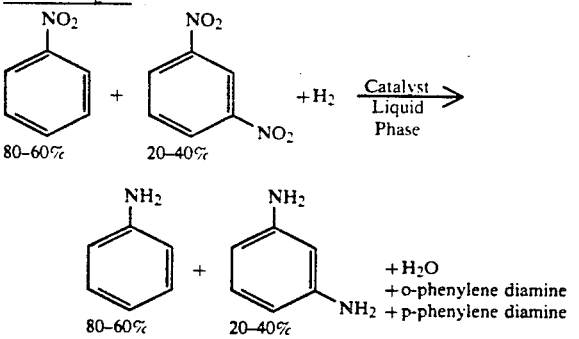

A primary advantage of the process of this invention is in the ability to proceed directly from benzene to the final aromatic mono- and diamino products without need for separation or isomer purification of the intermediate materials, i.e., the mononitrobenzene and dinitrobenzene. A further advantage is that because of the ability to carry out the first and second stage of the reaction in the liquid phase, it is possible to prepare the high melting m-phenylenediamine in existing relatively low-cost processing equipment. This eliminates the need for specialized equipment to prepare the high melting materials. Accordingly, it is possible to produce what heretofore have been "specialty chemicals" or chemicals requiring special processing as a co-product of commercial aniline production. This two-stage process, provides substantial commercial advantages. A further important advantage is that in using the counter-current flow of reactants in the first stage of the process, i.e., the mononitrobenzene and mixture of dilute nitric and dilute sulfuric acid, between the two reactors greater efficiencies and shorter processing times are possible, reducing the energy consumption of the process.

While the invention is being described primarily with reference to the co-production of aniline and m-phenylenediamine, it will be apparent to those skilled in the art that the process can be utilized to produce analogous monoamino and diamino compounds directly from a derivative of benzene, with the intermediate nitro and dinitro products being formed. As will also be recognized by one skilled in the art, the processing conditions can be varied to provide more highly nitrated compounds by increasing the amount of nitric acid and sulfuric acid utilized in the first stage of the reaction.

Presently Preferred Embodiments.

Figure 2:
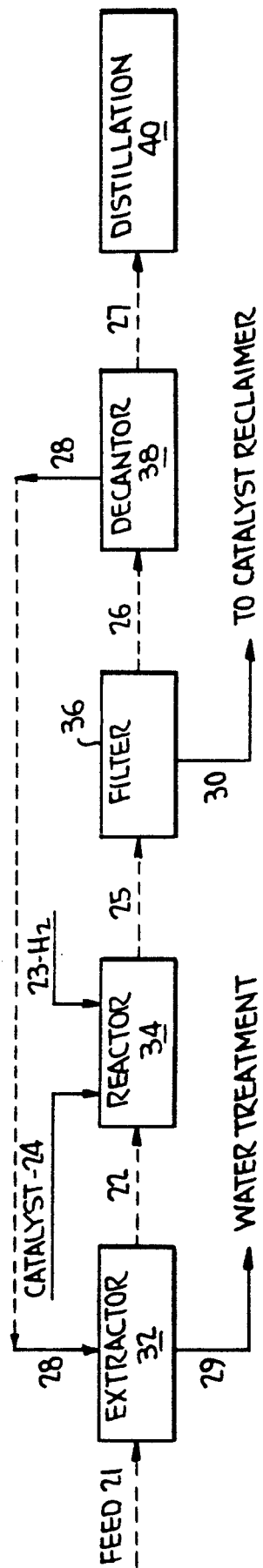
Figure 3:
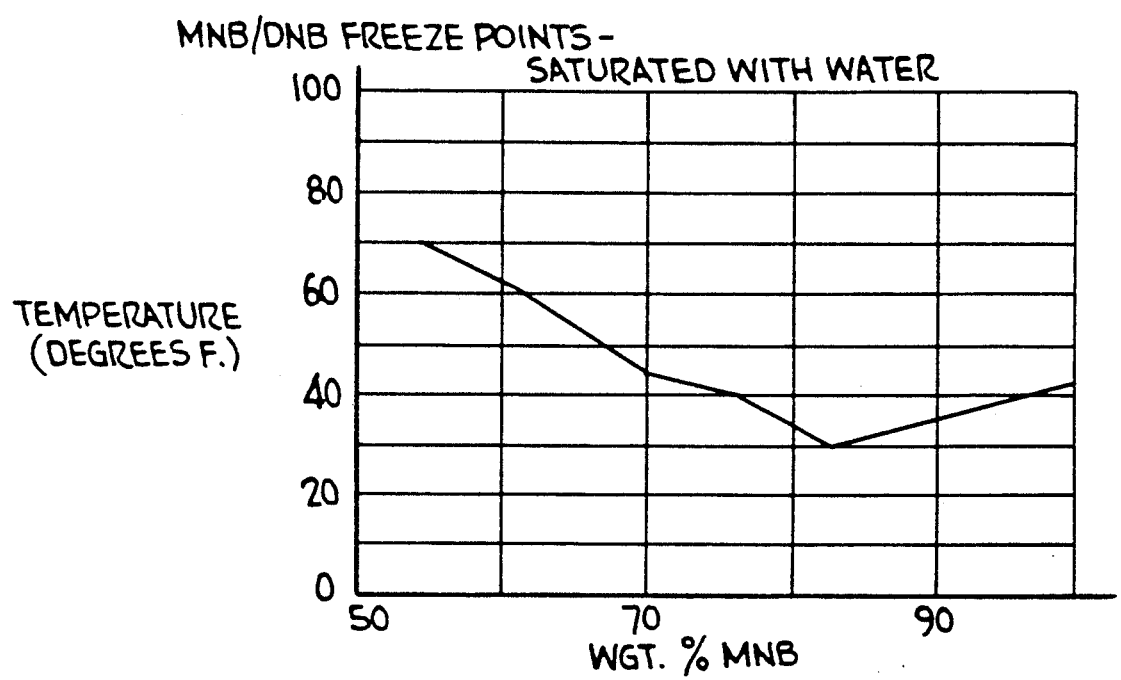

Having described the invention in general terms, presently preferred embodiments will be set forth in reference to the drawing wherein FIG. 1 is a reactor scheme for the production of mononitro and dinitrobenzene from benzene or dinitrobenzene from mononitrobenzene according to the first stage of the process of the present invention;

FIG. 2 is a schematic representing the liquid phase hydrogenation of nitrobenzenes according to the second stage of the process of the present invention; and FIG. 3 is a freezing point curve of mixtures of mononitro and dinitrobenzene saturated with water.

In the preferred embodiments, parts are by weight unless otherwise specified.

Referring first to FIG. 1 of the drawing, the reactor system utilized in the first stage of the process of this invention comprises a plurality of reactors 3, 6, and 8 for carrying out a continuous, liquid-phase nitration process. This reactor system includes the reactors needed for the production of dinitrobenzene directly from benzene. However, the system can also be operated as described hereinafter in Example 1 utilizing mononitrobenzene as the primary feed to produce dinitrobenzene. Further, two such systems can be used in combination, as described hereinafter in Example 2, to produce mononitrobenzene and dinitrobenzene directly from benzene. The entire system is constructed of stainless steel. Further, each reactor of the system contains an agitator, not shown, and the liquid within the reactors is well agitated throughout this stage of the process. Temperature control is maintained by internal heat-exchangers in each reactor, again not shown, as is conventional.

Referring now to FIG. 2 of the drawing, the hydrogenation system of the second stage of the process utilizes conventional batch reaction apparatus for a liquid phase reaction. More specifically, the hydrogenation or reduction system utilizes an extractor 32, batch reactor 34, filter 36, decantor 38 and distillation apparatus 40. The system employs conventional apparatus which is commercially available and known in the art for carrying out each step of the process. The system will be more fully described in the working examples.

Example 1

In a method of producing m-phenylenediamine from mononitrobenzene, referring to FIG. 1 of the drawing, sulfuric acid and nitric acid from inlets 1 and 2 are premixed and fed continuously into the first or main nitration reactor 3. .An organic stream 4 containing mostly nitrobenzene with minor quantities of benzene and dinitrobenzene is fed continuously from scrubber/nitration reactor 6 into the main nitration reactor 3 passing through separator centrifuge 5 where spent $H_2SO_4$ with trace amounts of $HNO_3$ are separated for regeneration. Most of the nitration of the mononitrobenzene occurs in the main nitration reactor 3. However, in the embodiment shown, an auxiliary reactor 8 is utilized for greater efficiency. Thus, a mixture containing mostly nitrobenzene, dinitrobenzene, $H_2SO_4$, and $H_2O$ with a small amount of $HNO_3$ flows continuously from reactor 3 through inlet 7 into the auxiliary nitration reactor 8 where the reaction is allowed to go to completion. The mixture of reaction product from reactor 8 is removed continuously and passed through centrifuge separator 9 where the dilute acid and nitrated products are separated. The nitrated products from centrifuge 9 consisting mostly of nitrobenzene and dinitrobenzene with some dissolved acid and by-products are washed with NaOH and $H_2O$ to remove the trace acids and oxidation by-products. The dilute acid from centrifuge 9 is sent continuously to the scrubber/nitration reactor 6 where it is reacted with a continuous fresh stream of mononitrobenzene, with a small amount of benzene added through inlet 11. Water is added through inlet 12 as needed to decrease the dilute acid concentration to approximately 70% $H_2SO_4$. The mixture from the scrubber/nitration reactor 6 is continuously removed passing through centrifuge separator 5 where the organics are separated from spent acid. The organic stream 4 flowing from separator 5 consisting mostly of mononitrobenzene containing a small amount of dinitrobenzene is sent to the main reactor 3 as stated above. The spent acid stream 10 from centrifuge separator 5 consisting mostly of 70% $H_2SO_4$ may be regenerated or used for other purposes.

In the embodiment shown, the nitration reaction is controlled to obtain about 70% mononitrobenzene and about 30% dinitrobenzene. However, it is possible and it may be desirable to control the ratio of mononitrobenzene and dinitrobenzene in the range of from about 60% to 80% mononitrobenzene and 40% to 20% dinitrobenzene. Within this ratio the reaction readily proceeds and it is not necessary to utilize special equipment or solvent means to avoid crystallization of the dinitrobenzene or to compensate for other characteristics of the dinitrobenzene. As illustrated in FIG. 3, a mixture of mononitrobenzene and dinitrobenzene within this range, saturated with water, is near a eutectic point in the freeze point curve. This permits nitration in one step without utilizing extra extraction or without an added solvent. Further, the same solution of the nitrobenzene and dinitrobenzene can be hydrogenated in the described system. The amount of conversion of nitrobenzene to dinitrobenzene can be controlled within the desired range by adjusting the sulfuric acid and nitric acid feed or by adjusting the nitrobenzene feed to reactor 3.

The system illustrated in FIG. 1 was started up by filling vessel 6 and vessel 3 with mononitrobenzene and 70% $H_2SO_4$ containing some $HNO_3$. A feed of mononitrobenzene with 5% benzene was fed to the scrubber/nitration reactor 6, and a pre-calculated amount of $H_2SO_4$ (98%) and nitric acid (63%) was fed to the main nitrator 3. The rates of feed of the mononitrobenzene, $H_2SO_4$, and $HNO_3$ were adjusted to get the desired product composition. Throughout this process the composition of the spent acid from the scrubber/nitration reactor 6 was adjusted to 70% by addition of water. This adjustment is necessary in order to maintain a low level of dinitrobenzene in the spent acid. The system was sampled every hour for organic and acid composition and feed rates were adjusted for the desired results. The temperature of the reactors were controlled for the desired results throughout the reaction. The feed rates, temperature, and compositions were then recorded as the optimum conditions for the reactor system. The optimum feed rate was 3.2 parts mononitrobenzene, 3.18 parts $H_2SO_4$ (98%), and 1.0 parts $HNO_3$ (63%).

The organic product of the reaction at reactors 3 and 8 consisted of mononitrobenzene (65%) and dinitrobenzene (35%). A small amount of acid was contained in the organic product. The dilute acid after passing through separator 9 had the composition of $H_2SO_4$, 77.7%; $HNO_3$, 0.8%; $H_2O$, 16.3%; nitrobenzene, 2.4%; and dinitrobenzene, 2.8%. The spent acid from the scrubber/nitration reactor 6 contained 72.5% $H_2SO_4$, 0.04% $HNO_3$, and traces of mononitrobenzene and dinitrobenzene. The organic feed from the scrubber/nitration reactor 6 to the main nitration vessel 3 consisted of nitrobenzene, 91.9%, dinitrobenzene, 4.6%, and benzene, 3.5%. The temperatures of the reactors at the optimum conditions were controlled at 42° C. for the scrubber/nitration reactor 6, 53° C. for the main nitration reactor 3, and 55° C. for the auxiliary nitration vessel 7. The amount of nitrobenzene to dinitrobenzene was easily controlled within the desired range of 60% to 80% mononitrobenzene and 40% to 20% dinitrobenzene by adjusting the sulfuric and nitric feed, or by adjusting the mononitrobenzene feed to reactor 3. No crystallization of dinitrobenzene was observed during this process. The by-product acid contained only traces of organic residue. The mononitrobenzene/dinitrobenzene product was ready for reduction after NaOH/water wash.

Referring now to FIG. 2 for the second stage of the process according to this invention, the hydrogenation process utilizes the liquid reaction product from the first stage of the process without prior separation or purification. The liquid reaction product is reacted with hydrogen in the presence of a catalyst followed by filtration, decantation and distillation of the crude second stage reaction product.

A typical feed composition to the hydrogenation reactor contains benzene, mononitrobenzene, dinitrobenzene (all isomers), phenylenediamine (all isomers) and aniline. The aniline and diamine are from the extraction carried out in extractor 32. The first stage reaction product feed is used to extract the nitrogen containing products from the water of the previous reduction reaction, i.e. the water layer recovered from decantor 38. The extracted water is then decanted off and pumped to a water treatment system. This extraction utilizes the reaction product feed to remove practically all amine compounds from the water stream.

The mononitrobenzene and dinitrobenzene mixture feed is then charged to reactor 34. Preferably, a stainless steel batch reactor with a suitable agitation system is utilized. Internal cooling coils or an external cooling loop can be provided to remove the heat of the reaction.

A steam jacket or other conventional means can be provided for heating the reactor to initiate the reaction. The reactor agitator is started following the feed of the reaction mixture to the reactor. Thereafter, a powder catalyst is added to the reactor. The catalyst is preferably added to the reactor in the form of a slurry. The reaction vessel is then padded/depadded to 40 psig with nitrogen three times to remove oxygen. This procedure is repeated with hydrogen and then the vessel is padded to 60 psig with hydrogen to start the reaction. The temperature range of the reaction is from about 140° to 302° F. (60° to 150° C.). Once the temperature reaches the desired reaction level, preferably about 248° F. (120° C.), the reactor pressure is raised to the preferred maximum pressure for the reaction. The pressure of the reactor preferably is above about 50 psig, and more preferably from 100 to 500 psig. Cooling water in the jacket of the reactor is used to control the exotherm of the reaction. Once the reaction stops using hydrogen, the reaction vessel is sampled to check for completion of the reaction. The operation of the reactor is preferably at about 248° F. (120° C.). The preferred feed composition to the reactor is from 70/25 to 70/30 of mononitrobenzene to dinitrobenzene. The dinitrobenzene isomers are present in the approximate amount of 88% meta, 10% ortho and 2% para. The catalyst is preferably a 5% palladium-on-carbon powder catalyst. The hydrogen is preferably free of inert materials to avoid interruption of the reaction. If inerts are present, the inerts will build up in the reactor head space thereby reducing the effective partial pressure of hydrogen in the reactor, resulting in a slower reaction time. If impure hydrogen is utilized, periodic purging of the reactor should be conducted to reduce the level of inerts and increase the reaction rate.

Following completion of the reaction, the crude reaction product is passed through a filter 36 to remove the catalyst from the reaction product. A sintered metal filter of a suitable micron size, such as 2 microns, is preferably utilized to remove the catalyst. Additionally, one or more filter bags can be positioned downstream of the metal filter to remove any catalyst fines. The filter inlet temperature should be a maximum of 248° F. (120° C.). The flow to the filter should be controlled on the inlet side with the delta P being monitored. The maximum delta P across the filter should be limited to 40 psig before the filter is unloaded. The recovered catalyst can then be collected from the filter for reuse. The filter serves to recover generally from 80% to 95% of the catalyst utilized.

Following filtration, the crude reaction product is subjected to decantation by any conventional means to recover the filtrate for subsequent distillation. As noted above, the water of reaction from decantor 38 is fed to extractor 32 to remove any amine products from the water prior to the water being passed to water treatment.

Following decantation, the reactor product is distilled using conventional distillation methods and apparatus. The distillation should avoid exposure of the reactor product to air since exposure to air at reduced pressure conditions can lead to increased tar formation and subsequent yield loss.

Table I below sets forth the processing of a 1,000-gallon 70/30 feed of mononitrobenzene and dinitrobenzene according to the second stage of the process of the present invention for producing aniline and m-phenylenediamine. The 70/30 feed mixture was produced according to the first stage of the process of the present invention. The stream numbers set forth in Table I correspond to the streams shown in FIG. 2. The catalyst utilized was present in the amount of 0.01 wt. % based on the total product feed to the reactor. The pressure of the reaction was 250 psig.

TABLE I

| STREAM COMPONENT | 21 LBS | 22 LBS | 23 LBS | 24 LBS | 25 LBS | 26 LBS | 27 LBS | 28 LBS | 29 LBS | 30 LBS |
|---|---|---|---|---|---|---|---|---|---|---|
| MNB[1] | 7700 | 7700 | | | | | | | | |
| DNB[2] | 3300 | 3300 | | | | | | | | |
| H2[3] | | | 611.3 | | | | | | | |
| CATALYST | | | | 1.1 | 1.1 | | | | | 1.1 |
| MPD[4] | | 28.2 | | | 1895.5 | 1895.5 | 1866.7 | 28.8 | 0.6 | |
| OPD[5] | | | | | 212.1 | 212.1 | 212.1 | | | |
| PPD[6] | | | | | 42.4 | 42.4 | 42.4 | | | |
| H2O | | | | | 3667.9 | 3667.9 | 785.6 | 2882.3 | 2882.3 | |
| ANILINE | | 86.4 | | | 5908.3 | 5908.3 | 5821.8 | 86.5 | 0.06 | |
| TOTAL LBS | 11000 | 11114.6 | 611.3 | 1.1 | 11727.3 | 11726.2 | 8728.6 | 2997.6 | 2883.0 | 1.1 |
| GALLONS | 1000 | 1020 | | | 1413 | 1413 | 1050 | 361 | 347 | |
| SCF[7] | | | 109732 | | | | | | | |

[1] mononitrobenzene
[2] dinitrobenzene
[3] hydrogen
[4] m-phenylenediamine
[5] o-phenylenediamine
[6] p-phenylenediamine
[7] standard cubic feet As noted above, the preferred catalyst for the second stage of the reaction is a 5% palladium-on-carbon catalyst. Table II sets forth the catalyst activities of various commercially available palladium-on-carbon catalysts in the hydrogenation of a mononitrobenzene/dinitrobenzene feed. It has been found that the palladium-on-carbon catalyst even at low catalyst concentrations provides for advantageous effects on the hydrogenation reaction.

TABLE II

| | Catalyst Activities[a] | | |
|---|---|---|---|
| Manufacturer | Catalyst Type | Lot | Reaction Time, hr[b] |
| Degussa | E101 O/W | 4003871162 | 3.3 |
| Degussa | E101 N/W | 99138/87 | 3.1 |
| Degussa | E101 R/W | SP-1-80 | 2.5 |
| Degussa | E196 R/W | 99056/85, 7914 | 1.9 |
| Englehard | Escat 10 | — | 2.6 |
| Englehard | Escat 11 | — | 3.0 |

TABLE II-continued

| | Catalyst Activities[a] | | |
|---|---|---|---|
| Manufacturer | Catalyst Type | Lot | Reaction Time. hr[b] |
| Johnson Matthey | 21R | BD40312-01 | 2.9 |

[a]Each experiment was run with 190 g of a 71/29 MNB/DNB feed and 0.04875 g (0.026 wt. % of feed) of catalyst (on a dry basis) at 100° C. and 250 psig.
[b]Time at reaction temperature (100° C.) during gas absorption.

The effect of the catalyst concentration on the reaction rate is summarized in Table III below.

TABLE III

| | | | Effect of Catalyst Concentration[a] | | | |
|---|---|---|---|---|---|---|
| | | | Catalyst | | | |
| Feed MNB/DNB | Temp, °C. | Pressure, PSIG | Type | Wt, g | Wt % of Feed | Time, hr.[b] |
| 71/29 | 100 | 250 | Degussa E196 R/W | 0.017 | 0.0089 | 7.5 |
| | | | | 0.023 | 0.012 | 4.8 |
| | | | | 0.030 | 0.016 | 3.7 |
| | | | | 0.049 | 0.026 | 1.9 |
| 71/29 | 120 | 250 | Degussa E196 R/W | 0.013 | 0.0068 | 6.0 |
| | | | | 0.017 | 0.0089 | 4.1 |
| | | | | 0.034 | 0.018 | 1.7 |
| 72/28 | 100 | 100 | Degussa E101 O/W | 0.074 | 0.039 | 6.8 |
| | | | | 0.245 | 0.129 | 5.0 |
| 72/28 | 100 | 200 | Degussa E101 O/W | 0.0325 | 0.017 | 5.0 |
| | | | | 0.065 | 0.034 | 3.0 |
| | | | | 0.130 | 0.068 | 2.8 |
| 72/28 | 100 | 300 | Degussa E101 O/W | 0.0217 | 0.011 | 6.5 |
| | | | | 0.0275 | 0.014 | 5.0 |

[a]Each experiment was run with 190 g of MNB/DNB feed.
[b]Time at specified reaction temperature during gas absorption.

The effect of pressure on the reaction rate is summarized below in Table IV.

TABLE IV

| | Effect of Pressure[a] | | |
|---|---|---|---|
| Pressure, psig | Catalyst Wt. g | Wt % Feed | Time, hr.[b] |
| 100 | 0.133 | 0.070 | 5.0 |
| 200 | 0.133 | 0.070 | 2.8 |
| 300 | 0.0217 | 0.011 | 6.5 |
| 300 | 0.0275 | 0.014 | 5.0 |
| 400 | 0.0220 | 0.012 | 6.0 |
| 500 | 0.0220 | 0.012 | 5.5 |
| 600 | 0.0220 | 0.012 | 5.0 |
| 800 | 0.0220 | 0.012 | 4.6 |

[a]Each experiment was run with 190 g of a 72/28 MNB/DNB feed at 100° C. with a Degussa E101 O/W catalyst.
[b]Time at reaction temperature during gas absorption.

Regarding the relation of the catalyst weight to the pressure, it can be seen that by raising the pressure, the amount of catalyst needed is reduced. Additionally, for given reaction temperature and pressure conditions, slight increases in the catalyst level reduce the cycle time. Once the optimum catalyst level is reached, further increases in the catalyst level will result in only slight increases in the reaction rate. The palladium-on-carbon catalyst is preferably utilized in the hydrogenation reaction in an amount of from 0.006 to 0.25 wt.% based on the total weight of the product feed. An efficient catalyst level was determined to be about 0.015 wt. % based on the weight of the total product feed at 250 psig and 212° F. (100° C.).

While palladium-on-carbon is the preferred catalyst and provides improved reaction conditions and results, it will be apparent to those skilled in the art that other conventional catalysts can also be used with the second stage of the present invention, such as those derived from a Group VIII metal. The metal catalyst can be used alone or with a carrier, such as carbon.

Example 2

This embodiment was carried out utilizing two reaction apparatus designed similar to the system shown in FIG. 1. The embodiment was run so as to produce dinitrobenzene (30-35%) from mononitrobenzene in Reactor System I and mononitrobenzene from benzene in Reactor System II. The by-product acid from reactor System I was used as feed acid for the mononitration (System II), and the mononitrobenzene produced in System II was used as feed for the dinitration (System I). Hence, the counterflow method, as described earlier, was obtained. System II was started up and brought to equilibrium as described in Example 1. The main reactor of System I was charged continuously with 4.03 parts mononitrobenzene, 3.18 parts $H_2SO_4$ (98%), and 1.0 parts $HNO_3$ (63%). The system was well agitated at 58° C. The organic product was composed of mononitrobenzene (65%) and dinitrobenzene (35%), with trace amounts of acids and oxidation by-products. The by-product acid from this System I was fed continuously into System II with 1.05 parts benzene, and extra acid of the composition 1.35 parts $HNO_3$ (63%) and 1.0 parts $H_2SO_4$ (98%). The system was well agitated at 55° C. The product of this reaction was composed of mostly mononitrobenzene with trace amounts of benzene and acid. This product can now be used as feed for dinitration in System I.

Example 3

In an analogous process to the process of Example 2, benzene was replaced with toluene. The toluene was first nitrated, and the nitration products hydrogenated as in Example 2 to produce mixed toluidine isomers and mixed toluene diamine isomers. The composition of the reaction is controlled to provide the desired ratios of products.

Example 4

In the process of Example 1, the mononitrobenzene was replaced with o-nitrotoluene and nitrated as in Example 1. The nitrated product consisting mostly of o-nitrotoluene, 2,4-dinitrotoluene and 2,6-dinitrotoluene was then hydrogenated, as described in Example 1, to produce o-toluidine, 2,4-toluenediamine, and 2,6- toluenediamine. The composition of the reactants is controlled to provide the desired ratios of products.

In Example 1 of this application mononitrobenzene was primarily fed to scrubber/nitration reactor 6 in place of benzene. In Example 2 to describe the countercurrent flow technique of the preferred embodiment of this invention, two separate reactor systems essentially as shown in FIG. 1 were utilized in combination. The system of FIG. 1, however, can be used as illustrated in a continuous process to produce mononitrobenzene and dinitrobenzene in controlled amounts directly from benzene. The system was utilized as in Examples 1 and 2 in order to more conveniently illustrate the characteristics of the disclosed invention. Also in accordance with the present process, as shown in Examples 3 and 4, a benzene derivative can be substituted for benzene to co-produce mono- and diamines. In the process, the benzene or benzene derivative will have the structure

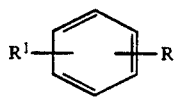

wherein R and $R^1$ are each hydrogen or alkyl having from 1 to 5 carbon atoms.

The presently disclosed process permits operation within advantageous temperature ranges. Specifically, the nitration reactions can advantageously be carried out at from about 30° to 85° C., and preferably where a plurality of reactors are employed the scrubber/nitration reactor will be at a temperature of from about 35° to 55° C.; the main nitration reactor at from about 40° to 70° C., and, if utilized, the auxiliary nitration reactor will be at a temperature of from about 45° to 70° C. The second stage of the process is preferably carried out in a temperature range of from about 140° to 302° F. (60° to 150° C.) with the most preferred temperature being approximately from about 248° to 302° F. (120° to 150° C.).

An additional important advantage of the counterflow process herein described is in the nature of the by-products. The dinitration of benzene will produce a spent acid which contains large amounts of dinitrobenzene, phenolic compounds, and other oxidized by-products. When starting with benzene and utilizing the countercurrent flow method, as described as a preferred embodiment of this invention, a spent acid is produced which is substantially equivalent to the spent acid obtained in a mononitration process. This spent acid is "clean" and substantially easier to work with in a recovery process—for example, by re-concentration; or for direct use—for example, in a phosphoric acid plant.

A primary advantage of the hydrogenation reaction of the present invention is that the feedstock for the reaction is a liquid. This permits the direct utilization of the liquid reaction product of the nitration stage of the process. The reduction of the mononitro compounds produces less heat per mole and moderates the reaction temperature. Further, the large amount of monoamine in the reactor product extracts most of the water-soluble diamines from the water of reaction, which simplifies the purification of the final product. Just as the monoamine causes the diamine to be extracted from the reaction water, it also prevents the water from being highly soluble in the organic phase and precludes the need to distill out large amounts of water in the purification process. This feature leads to substantial energy savings and allows smaller distillation equipment for a given amount of product. The aforesaid and other advantages of the co-production process of the present invention are apparent from the above disclosure.

As will be apparent to one skilled in the art, various modifications can be made within the scope of the aforesaid description. Such modifications being within the ability of one skilled in the art form a part of the present invention and are embraced by the appended claims.

It is claimed:

1. A continuous two-stage process for the co-production of aniline and m-phenylenediamine by the direct nitration of benzene comprising the steps of
   (A) in a first stage reacting benzene with a mixture of nitric acid and sulfuric acid, said reaction being controlled to provide a mixture of from about 60% to about 80% mononitrobenzene and 40% to 20% dinitrobenzene;
   (B) in a second stage subjecting said mixture of mononitrobenzene and dinitrobenzene of step (A) to a liquid phase hydrogenation reaction comprising contacting said mixture in the liquid phase with hydrogen in the presence of a catalyst to provide a mixture containing about 60% to about 80% aniline and about 40% to about 20% m-phenylenediamine; and
   (C) separating said aniline and m-phenylenediamine from said mixture.

2. The process of claim 1 wherein in said first stage benzene is reacted with said nitric and sulfuric acid in two steps, wherein in the first of said two steps a mixture of concentrated sulfuric and nitric acid is reacted with mononitrobenzene to provide a mixture of about 60% to about 80% mononitrobenzene and about 40% to about 20% dinitrobenzene and dilute sulfuric and nitric acids; separating said mononitrobenzene and dinitrobenzene from said acid mixture and then reacting in the second of said two steps said dilute nitric and sulfuric acid with benzene to provide mononitrobenzene, and using said mononitrobenzene in said first of said two steps.

3. The process of claim 1 wherein said nitration of benzene is controlled whereby said mixture of mononitrobenzene and dinitrobenzene is present at about 70% mononitrobenzene and about 30% dinitrobenzene.

4. The process of claims 2 or 3 wherein said mixture of mononitrobenzene and dinitrobenzene is separated from said dilute acid mixture by centrifugation or decantation.

5. The process of claim 1 wherein said catalyst of step (B) is a palladium-on-carbon catalyst.

6. The process of claim 5 wherein said catalyst is present in an amount from 0.006 to 0.25 wt. % based on the total weight of said mixture of mononitrobenzene and dinitrobenzene.

7. The process of claim 2 wherein the temperature in the first of said two steps is at from about 40° to 70° C.

8. The process of claim 2 wherein the temperature in the second of said two steps is at from about 35° to 55° C.

9. The process of claim 7 wherein said first of said two steps is carried out in two stages in a main reactor and an auxiliary reactor, and the temperature in the main reactor is at from about 40° to 65° C. and the temperature in the auxiliary reactor is at from about 45° to 70° C.

10. The process of claim 1 wherein the temperature of said hydrogenation reaction is at from about 60° to about 150° C.

11. A continuous two-stage process for the co-production of an aromatic monoamine and an aromatic diamine by the direct nitration of benzene or a benzene derivative comprising the steps of
(A) in a first stage reacting a benzene compound having the formula

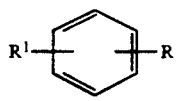

wherein R and R¹ are each hydrogen or alkyl of from 1 to 5 carbon atoms, with a mixture of nitric acid and sulfuric acid, said reaction being controlled to provide a mixture of from about 60% to about 80% of the mononitro compound and 40% to 20% dinitro compound;
(B) in a second stage subjecting said mixture of mononitro and dinitro compounds of step (A) to a liquid phase hydrogenation reaction comprising contacting said mixture in the liquid phase with hydrogen in the presence of a catalyst to provide a mixture containing about 60% to about 80% of the aromatic monoamine and about 40% to about 20% of the aromatic diamine; and
(C) separating said aromatic monoamine and aromatic diamine from said mixture.

12. The process of claim 11 wherein in said first stage said benzene compound is reacted with said nitric and sulfuric acid in two steps, wherein in the first of said two steps a mixture of concentrated sulfuric and nitric acid is reacted with the mononitrobenzene compound to provide a mixture of about 60% to about 80% mononitrobenzene compound and about 40% to about 20% dinitrobenzene compound and dilute sulfuric and nitric acids; separating said mononitrobenzene compound and dinitrobenzene compound from said acid mixture and then reacting in the second of said two steps said dilute nitric and sulfuric acid with said benzene compound to provide the mononitrobenzene compound, and using said mononitrobenzene compound in said first of said two steps.

13. The process of claim 11 wherein said nitration of said benzene compound is controlled whereby said mixture of mononitrobenzene compound and dinitrobenzene compound is present at about 70% mononitrobenzene compound and about 30% dinitrobenzene compound.

14. The process of claims 12 or 13 wherein said mixture of said mononitrobenzene compound and dinitrobenzene compound is separated from said dilute acid mixture by centrifugation.

15. The process of claim 11 wherein said catalyst of step (B) is a palladium-on-carbon catalyst.

16. The process of claim 15 wherein said catalyst is present in an amount from about 0.006 to 0.25 wt. % based on the total weight of said mixture of mononitrobenzene and dinitrobenzene.

17. The process of claim 11 wherein the temperature in the first of said two steps is at from about 40° to 70° C.

18. The process of claim 11 wherein the temperature in the second of said two steps is at from about 35° to 55° C.

19. The process of claim 17 wherein said first of said two steps is carried out in two stages in a main reactor and an auxiliary reactor, and the temperature in the main reactor is at from about 40° to 65° C. and the temperature in the auxiliary reactor is at from about 45° to 70° C.

20. The process of claim 11 wherein the temperature of the hydrogenation reaction is at from about 60° to about 150° C.

21. A continuous process for the co-production of aniline and m-phenylenediamine from an unpurified mixture of from about 60% to about 80% mononitrobenzene and 40% to 20% dinitrobenzene recovered from a benzene nitration process comprising subjecting said mixture of mononitrobenzene and dinitrobenzene to a liquid phase hydrogenation reaction comprising reacting said mixture in the liquid phase with hydrogen in the presence of a catalyst to provide a mixture containing about 60% to about 80% aniline and about 40% to about 20% m-phenylenediamine, and separating said aniline and m-phenylenediamine from said mixture.

22. The process of claim 21 wherein said catalyst is a palladium-on-carbon catalyst present in an amount of from about 0.006 to 0.25 wt. % based on the total weight of said mixture of mononitrobenzene and dinitrobenzene.

23. The process of claim 21 wherein the temperature of the hydrogenation reaction is from about 60° to about 150° C.

* * * * *